(12) United States Patent
Laitala et al.

(10) Patent No.: US 7,729,582 B2
(45) Date of Patent: Jun. 1, 2010

(54) FIBRE OPTIC CABLE AND METHOD FOR PRODUCING THE SAME

(75) Inventors: Ville Laitala, Turku (FI); Pauli Salmelainen, Turku (FI)

(73) Assignee: Wallac Oy, Turku (FI)

( * ) Notice: Subject to any disclaimer, the term of this patent is extended or adjusted under 35 U.S.C. 154(b) by 14 days.

(21) Appl. No.: 12/097,789

(22) PCT Filed: Dec. 7, 2007

(86) PCT No.: PCT/FI2007/050669

§ 371 (c)(1),
(2), (4) Date: Jun. 17, 2008

(87) PCT Pub. No.: WO2008/068388

PCT Pub. Date: Jun. 12, 2008

(65) Prior Publication Data

US 2008/0260335 A1 Oct. 23, 2008

Related U.S. Application Data

(60) Provisional application No. 60/873,587, filed on Dec. 8, 2006.

(30) Foreign Application Priority Data

Dec. 8, 2006 (FI) .................................. 20065786

(51) Int. Cl.
*G02B 6/44* (2006.01)
(52) U.S. Cl. ........................................ 385/100; 65/410
(58) Field of Classification Search .................... 385/9, 385/53, 55, 56, 58, 76, 78, 92
See application file for complete search history.

(56) References Cited

U.S. PATENT DOCUMENTS

| 3,554,721 | A |   | 1/1971 | Gardner |
|-----------|---|---|--------|---------|
| 3,674,452 | A | * | 7/1972 | Strack .......................... 65/410 |
| 4,116,655 | A |   | 9/1978 | Lewis |
| 4,332,439 | A |   | 6/1982 | Luebbers et al. |

(Continued)

FOREIGN PATENT DOCUMENTS

DE        4332439 C1 *  5/1995

(Continued)

*Primary Examiner*—Charlie Peng
*Assistant Examiner*—Peter Radkowski
(74) *Attorney, Agent, or Firm*—Young & Thompson (57) ABSTRACT

The present technology relates generally to fibre optic cables their manufacture and uses in the field of optical measurements including biochemical laboratory instrumentation for measuring properties of samples on microtitration plates and corresponding sample supports. The technology has also applications in various laser technologies. A fibre optic cable has an active surface with a determined form provided at a first optical interface at the first end of the cable. The first end of the cable is fused into an exemplary circular form, the fused cable end including fibre ends both within the active surface and outside the active surface. At the opposite, second end of the cable, those fibres which have their first ends at the determined active surface area, are used for forming a second optical interface. It is possible to have high transmission efficiency in optical interfaces where other than circular cross section of the light beam exists.

19 Claims, 7 Drawing Sheets

U.S. PATENT DOCUMENTS

| | | | |
|---|---|---|---|
| 4,630,923 A * | 12/1986 | Tans et al. | 356/301 |
| 4,666,245 A * | 5/1987 | Pointer | 385/115 |
| 4,815,816 A * | 3/1989 | Schneider | 385/116 |
| 4,932,747 A | 6/1990 | Russell | |
| 4,952,022 A * | 8/1990 | Genovese | 385/116 |
| 5,017,772 A | 5/1991 | Hafle | |
| 5,233,679 A * | 8/1993 | Oyama | 385/146 |
| 5,453,838 A * | 9/1995 | Danielian et al. | 356/600 |
| 5,550,945 A * | 8/1996 | Gregory | 385/116 |
| 5,661,837 A | 8/1997 | Yamamoto | |
| 5,844,239 A * | 12/1998 | Kimura | 250/341.8 |
| 6,101,703 A | 8/2000 | Odanaka | |
| 6,118,521 A * | 9/2000 | Jung et al. | 356/73 |
| 6,222,620 B1 * | 4/2001 | Jung et al. | 356/73 |
| 6,233,047 B1 * | 5/2001 | Jung et al. | 356/73 |
| 6,239,868 B1 * | 5/2001 | Jung et al. | 356/73 |
| 6,246,479 B1 * | 6/2001 | Jung et al. | 356/419 |
| 6,301,412 B1 | 10/2001 | Mori et al. | |
| 6,349,160 B2 * | 2/2002 | Tsien et al. | 385/35 |
| 6,406,641 B1 | 6/2002 | Golzarian | |
| 6,870,616 B2 * | 3/2005 | Jung et al. | 356/326 |
| 7,031,579 B2 * | 4/2006 | Sisodia et al. | 385/120 |
| 7,142,290 B2 * | 11/2006 | Tsien et al. | 356/72 |
| 2003/0202760 A1 * | 10/2003 | Henze et al. | 385/115 |

FOREIGN PATENT DOCUMENTS

| | | |
|---|---|---|
| EP | 0 237 850 A1 | 9/1987 |
| EP | 0 903 571 A2 | 3/1999 |
| GB | 1 319 879 A | 6/1973 |
| GB | 2 191 873 A | 12/1987 |
| GB | 2191873 A * | 12/1987 |
| GB | 2 283 105 A | 4/1995 |

\* cited by examiner

FIBRE OPTIC CABLE AND METHOD FOR PRODUCING THE SAME

FIELD OF TECHNOLOGY

The present technology relates generally to fibre optic cables, their manufacture and uses. Especially the present technology relates to what is disclosed in the preamble of the independent claims.

BACKGROUND

Fibre optic cables are widely used in optical instruments. They are practical means for guiding light for illumination and light to be measured. Fibre optic cables usually consist of a large number of thin fibres, to make the cable flexible. Each fibre usually has a cladding which is made of material with a lower refractive index than the core material of a fibre. The cladding enables total reflection at the interface between the core and the cladding of the fibre. The number of fibres and the diameter of fibres depend on application. The number of fibres is often in the range of 50-500, and the diameter of each fibre is often in the range of 50-600 μm, but numbers and diameters of fibres beyond these ranges are also quite possible. In many applications it is important to achieve small transmission loss of light. When light is applied at an end of a fibre optic cable, only part of the light enters the fibres. One reason for the losses in the optical interface is that part of the applied light enters the spaces between adjacent fibres at the surface of the cable end. This space between the individual fibres can be reduced by fusing the ends of the fibre optic cable. The fusing is usually done by heating and pressing the bundle of fibres. Initially the fibres have circular cross sections, which become hexagonal when the fibre bundle has been fused. In order to avoid interspaces between the fibres, it is useful to avoid using attachment glue or cement in fusing.

In the fusing it is necessary to apply a pressure on the fibre bundle in order to remove the hollow spaces between fibres and to achieve a cable end with small loss of light intensity. It is useful to use a constant pressure to each point of the transversal outline of the bundle. When the bundle has a circular outline, the bundle will remain its form during the fusing, which leads to a homogeneous optical interface with no aberration in the arrangement of the fibre ends. There are several methods for applying a constant pressure to circular fibre bundles of varying sizes. However, providing a fused bundle end with some other than circular outline would require special tools, which are designed for a specific bundle which has a determined diameter and determined number of fibres with determined diameters and materials. Also, achieving high homogeneity and other optical characteristics for a fused, non-circular bundle would be difficult if not impossible. Fusing can also be made by applying cohesive agent in between the fibres, but then the aim of removing the interspaces between the fibres is not at all achieved.

In many applications where optic cables are used, the object to be illuminated is not circular but has some other form, such as rectangular. Also, when light is received into an optic cable, the light source/emission source may have a non-circular form. Such situations are often encountered e.g. is the field of optical measurement equipment used in clinical laboratories. Basic operating principles of optical measurement of clinical samples are next briefly described.

The routine work and also the research work in analytical biochemical laboratories and in clinical laboratories is often based on different tags or labels coupled on macromolecules under inspection. The typical labels used are different radioactive isotopes, enzymes, different fluorescent molecules and e.g. fluorescent chelates of rare earth metals.

The detection of labels can be performed by utilizing its natural biochemical function, i.e. to alter the physical properties of molecules. In immunoassays colourless substances are catalysed into colourful substances or non-fluorescent substances are catalysed into fluorescent substances.

The colourful substances are measured with absorption, i.e. photometric measurement. In the photometric measurement the intensity of filtered and stabilized beam is first measured without any sample and then a sample inside a well of a sample plate is measured. The absorbance i.e. the absorption values are then calculated.

The fluorescent measurement is generally used for measuring quantities of fluorescent label substance in a sample. The most photoluminescence labels are based on molecular photoluminescence process. In this process optical radiation is absorbed by the ground state of a molecule. Due to the absorption of energy the quantum molecule rises into higher excited state. After the fast vibrational relaxation the molecule returns back to its ground state and the excess energy is released as a photon.

A further commonly used measurement method is chemiluminescence measurement where emission is due to a chemical reaction, and emission of a substance is measured from a sample without excitation by illumination. Thus a photoluminometer can also be used as a chemiluminometer.

The typical instruments in analytical chemical research laboratories are the different spectroscopic instruments. Many of them are utilizing ultraviolet (UV) visible or near infrared (NIR) region of electromagnetic spectrum. The instruments are most often multi-label plate readers, but they may also be may be spectrophotometers or spectrofluorometers. Such instruments may have one or two wavelength dispersion devices, such as monochromators. With a controllable dispersion device it is possible to perform the measurements throughout the required optical spectrum. To achieve efficient and accurate measurements of small samples, it is often necessary to maximize the intensity of excitation light at the sample, and to maximize the optical acquisition efficiency of the emission signal received from the sample.

A monochromator generally has a dispersive component and an input aperture and an output aperture for input and output light beams respectively. The output aperture also serves to select the light beam of determined wavelength from the light spectrum. An end of an optical cable can be coupled to an input aperture at a monochromator side wall. An end of another optical cable can be coupled to an output aperture at a monochromator side wall. The dispersive component spreads the light in different angles as a function of the wavelength of light, and therefore the transmittance band as a function of wavelength has round slopes if the monochromator has circular apertures. However, a narrow transmittance band with steep slopes would usually be desirable. In order to achieve a narrow transmittance band the aperture should be narrow. Therefore it is useful to use a slit as an aperture, wherein the slit is rectangular with the width smaller than the height. In order to reduce the attenuation of the light beam, it is also useful to have an input aperture of the same form as the output aperture.

A monochromator can potentially have a narrow transmittance band with steep slopes, and it is also possible to have stepless adjustment of the band pass wavelength, which is not possible with optical filters. However, due to the interface problems the transmission efficiency of the monochromator may low and the transmittance band as a function of wavelength is wide and has round slopes. Therefore optical filters are often used instead of monochromators in optical instruments.

Optical measurement instruments may also have other locations where a circular cross section of the transferred light beam is not suitable. For example, sample wells may have a rectangular shape, and light sources, such as flash lamps, may have a non-circular light emitting area.

There are also several other applications than optical measurement instruments where a circular cross section of a light beam is not suitable. For example, efficient lasers are used in industrial machining and welding purposes. The laser beam is generally guided from the laser source to the object via fibre optic cables. The light beam received from the end of the optic cable is directed to the surface of an object, wherein the beam has circular cross section. When the laser beam is moved along the object, the treated area forms a line on the object. When the laser beam has a circular cross section, less energy is applied to the edges of the treated line than to the centre of the treated line. However, it is often required to treat the object homogeneously within the whole treated area. For example, this is the case when removing oxides from metal surfaces with laser. Such a homogeneous treatment is not possible or it is complicated with a laser beam which has a circular cross section.

SUMMARY

A fibre optic cable, including a plurality of optic fibres, wherein the cable and each fibre have a first end and a second end, the cable has a first optical interface at the first cable end, and the cable has a second optical interface at the second cable end, and at the first end of the cable at least part of the first fibre ends are fused, the fused end forming at least part of the first optical interface of the cable, is characterized in that the first optical interface at the first end of the fibre optic cable has a determined active surface area, which includes ends of a first group of the fibres, the fibre optic cable comprises a second group of fibres, wherein the fibres of a second fibre group have their first ends outside said active surface area, and at least part of the fibres of a second fibre group have their first ends between the active surface and the outline of the first cable end, and at least part of the fibres have a non-coherent mutual arrangement between the first and second ends of the cable.

A fibre optic cable according to one implementation of the technology is characterized in that second fibre ends of said first group of fibres form at least part of the second optical interface of the cable.

A fibre optic cable according to another implementation of the technology is characterized in that t a determined active surface area is non-circular.

A fibre optic cable according to a further implementation of the technology is characterized in that the transversal outline of all fibre ends is circular at the first end of the cable.

A fibre optic cable according to a further implementation of the technology is characterized in that the space between individual fibre ends is reduced.

A fibre optic cable according to a further implementation of the technology is characterized in that the ends of at least one group of fibres are cut into shorter length than ends of at least one other group of fibres of the cable.

A fibre optic cable according to a further implementation of the technology is characterized in that the first fibre group and the second fibre group are both separate fibre bundles.

A fibre optic cable according to a further implementation of the technology is characterized in that at least two active surfaces are determined for the first optical interface at the first end of the cable, wherein a first group of fibres have their first ends within a first determined active surface and a second group of fibres have their first ends within a second determined active surface.

A fibre optic cable according to a further implementation of the technology is characterized in that the first and second active surfaces are overlapping, wherein the first fibre ends of the first and second fibre groups have mixed locations within the overlapping area of the active surfaces.

A fibre optic cable according to a further implementation of the technology is characterized in that the fibres of the second fibre group are shorter than the fibre optic cable, whereby the second fibre group serves as an auxiliary fibre group for a cable end without extending to the vicinity of the other cable end.

A fibre optic cable according to a further implementation of the technology is characterized in that the fused fibre ends are heat treated and/or pressure treated.

A fibre optic cable according to a further implementation of the technology is characterized in that the fibres of the first fibre group have a non-coherent mutual arrangement between the first and second ends of the first fibre group.

A fibre optic cable according to a further implementation of the technology is characterized in that the second optical interface is within a fused end at the second end of the fibre optic cable.

A fibre optic cable according to a further implementation of the technology is characterized in that the second optical interface has a determined active surface area, which includes all second ends of the fibres of the first fibre group.

A fibre optic cable according to a further implementation of the technology is characterized in that the second fibre ends of the fibres in the second fibre group are outside said active surface of the second optical interface.

A fibre optic cable according to a further implementation of the technology is characterized in that at least part of the second ends of the fibres of the second fibre group are adjacent to the second ends of the fibres of the first fibre group, wherein the second ends of the fibres of the first and second groups form an integral second end of the fibre optic cable.

A fibre optic cable according to a further implementation of the technology is characterized in that the second fibre ends of the first group of fibres form a second optical interface of the cable, and the second fibre ends of the second group of fibres form a third optical interface at the second cable end.

A fibre optic cable according to a further implementation of the technology is characterized in that the fibre optic cable has two branches which both have first ends, first optical interfaces, and first fibre groups, wherein the second ends of the two first fibre groups are connected to form a second end and at least one second optical interface of the fibre optic cable.

A fibre optic cable according to a further implementation of the technology is characterized in that the first fibre group has a first subgroup and a second subgroup wherein the first ends of the fibres in the first subgroup form a first active surface, the first ends of the fibres in the second subgroup form a second active surface, the second ends of the fibres in the first subgroup form a third active surface and the second ends of the fibres in the second subgroup form a fourth active surface.

A fibre optic cable according to a further implementation of the technology is characterized in that its second end is coupled with a second end of another cable according to the present technology, wherein the two cables form a combined cable which has two first ends, each of the first ends having an active surface with similar or different determined shapes and sizes.

A fibre optic cable according to a further implementation of the technology is characterized in that its first end is coupled to an input or an output of a monochromator.

A fibre optic cable according to a further implementation of the technology is characterized in that its one end is coupled to the proximity of a sample and another end is coupled to a detector.

A fibre optic cable according to a further implementation of the technology is characterized in that its one end is coupled to the proximity of a sample and another end is coupled to receive illumination from a light source.

A fibre optic cable according to a further implementation of the technology is characterized in that the first end of the cable is coupled to the proximity of a sample, one group of fibres at the second cable end is coupled to a detector, and another group of fibres at the second cable end is coupled to a light source.

A method for producing a fibre optic cable, wherein the method comprises providing at least one bundle of optic fibres and fusing fibre ends at least at a first end of the cable, is characterized in that at least one pattern of active surface is determined for the first end of the cable, wherein the active surface includes ends of a first group of the fibres, a second group of fibres is provided in the fibre optic cable, wherein the fibres of a second fibre group have their first ends outside said active surface area, and at least part of the fibres of a second fibre group have their first ends between the active surface and the outline of first cable end, at least part of the second optical interface of the cable is formed of second fibre ends of said first group of fibres, and at least part of the fibres are arranged mutually non-coherently between the cable ends.

A method according to one implementation of the technology is characterized in that fibre ends at the first end of the cable are illuminated based on the determined pattern, fibres at the second end of the cable are separated into said first and second groups based on the illumination at each fibre end at the second end of the cable, and at least part of the second optical interface of the cable is formed of second fibre ends of said separated first group of fibres, A method according to another implementation of the technology is characterized in that the illuminating comprises applying light onto the first end of the cable and applying a mask within the optical path of the light, said mask comprising an area with a form of the determined pattern of the active surface, and within said area of the mask the transmission characteristic of the light is different from the transmission characteristic of the light outside said area.

A method according to a further implementation of the technology is characterized in that the illuminating comprises applying light onto the second end of the cable and applying a mask at the first end of the cable, said mask comprising an area with a form of the determined pattern of the active surface, and within said area of the mask the reflection characteristic of the light is different from the reflection characteristic of the light outside said area.

A method according to a further implementation of the technology is characterized in that a first fibre bundle is provided as the first group of fibres, and the active surface is formed of the first ends of the fibres of the first bundle, a second fibre bundle is provided as the second group of fibres, and the first ends of the fibres of the second bundle are arranged outside the active surface, and a first cable end, including the first ends of the fibres of the first bundle and the first ends of the fibres of the second bundle, is fused.

A method according to a further implementation of the technology is characterized in that a further active surface is formed of the second ends of the fibres of the first bundle, second ends of the fibres of the second bundle are arranged outside the active surface, a second cable end, including the second ends of the fibres of the first bundle and the second ends of the fibres of the second bundle, is fused, thus forming the second optical interface of the cable.

A method according to a further implementation of the technology is characterized in that fibre ends of another group of fibres are cut into a length, which is shorter than ends of at least one other group of fibres.

A method according to a further implementation of the technology is characterized in that the fibres of the second fibre group are made shorter than the fibre optic cable, whereby the second fibre group serves as an auxiliary fibre group for a cable end without extending to the vicinity of the opposite cable end.

A method according to a further implementation of the technology is characterized in that the second ends of the first group of fibres are fused.

A method according to a further implementation of the technology is characterized in that in fusing fibre ends pressure is applied in radial direction on the longitudinal surface of the fibres in order to decrease or remove the interspaces between adjacent fibres.

A method according to a further implementation of the technology is characterized in that in fusing fibre ends heating is applied to the fibre ends.

The technology also concerns an optical measurement instrument for measuring samples, which is characterized in that it comprises a fibre optic cable according to the technology described herein.

An optical measurement instrument according one implementation of the technology is characterized in that the instrument comprises means for performing photoluminescence measurement, chemiluminescence measurement and/or photometric measurement of samples.

DETAILED DESCRIPTION

In this patent application term "light" means any electromagnetic radiation which can be transferred through optical fibres. It is thus not restricted in any way to the visible part of the light spectrum.

In this patent application term "fibre optic cable" means a bundle or several bundles of optical fibres, wherein the cable has at least two ends for optical interfaces.

In this patent application term "non-coherent" fibre optic cable means that the fibres within the cable are not in the same relative order in all locations along the cable. If the cable has at least one specific bundle of fibres, "non-coherent" may mean that the individual fibres within at least one bundle are not in the same relative order in all locations along the bundle. If a part of fibres of the cable is not led along the whole length of the cable between cable ends, the cable is considered non-coherent.

In this patent application term "active surface" means an area at the end of a fibre optic cable, which is used for transferring light in a normal use of the cable. One end of a cable may have more than one active surface. The active surface is normally transversal to the length of the cable. The "pattern" of the active surface includes the form and size of the active surface.

In this patent application "optical interface" of a fibre optic cable means a general boundary wherein light can be transmitted into fibres of the cable or received from fibres of the cable.

In this patent application term "fused" means that fibre ends have been treated with pressure and/or heating in order to reduce the interspaces between the fibres. In fusing, usefully both heating and pressure are applied. The pressure is usefully applied in a radial direction towards the fibres. The applied "pressure" usefully means a value of pressure that exceeds an ambient pressure.

In this patent application "photoluminescence" or "excitation" also includes such chemical processes within samples which are activated by applied light.

An object of the present technology is to provide a fibre optic cable for various applications, wherein the described problems of the known technology are avoided or reduced. The object of the technology is therefore to achieve a fibre optic cable wherein the active surface of the end of the cable has a predetermined cross section form, which can be other than circular. It is a further object of the technology to increase the optical transmission efficiency in applications where fibre optic cables are used.

The object of the technology is achieved by providing a fibre optic cable wherein an active surface with a determined form is provided at a first optical interface at the first end of the cable. The first end of the cable is fused into a circular form, the fused cable end including fibre ends both within the active surface and outside the active surface. At the opposite, second end of the cable, those fibres which have their first ends at the determined active surface area, are used for forming a second optical interface. This way it is possible to have high transmission efficiency in optical interfaces where other than circular cross section of the light beam exists.

It is useful that the fibres of a second fibre group have their first ends outside said active surface area, and at least part of the fibres of a second fibre group have their first ends between the active surface and the outline of first cable end, This way it is possible to provide an outline for the cable end which is suitable for fusing.

According to one embodiment of the technology a fibre optic cable according to the technology is produced by first illuminating a first end of a fibre optic cable based on the determined active surface, and separating the fibres at the second end of the cable on the basis of the illumination received at each of the fibre ends. One group of the separated fibres is then used for forming another fused end for the cable.

According to another embodiment of the technology a fibre optic cable according to the technology is produced by providing at least two bundles of fibres, wherein the ends of first fibre bundle are used for forming the active surface of at least the first optical interface. The fibre ends of at least one other bundle are used for providing a complementing the cable end into a form that has a circular outline. Such a cable end can then be fused. It is possible to use the second ends of the first fibre bundle for forming an active surface of a same or other predetermined form to the second optical interface as well. Ends of other fibres can be used to complement the second end into a circular form before fusing the second end. With this embodiment of the technology it is possible to produce fibre optic cables which have active surfaces of determined shape in both ends of the cable.

The present technology provides solutions for the problems of the earlier technology. It is possible to determine any required pattern for the active fibre ends of a cable according to the technology. The intensity of transferred light is retained with small attenuation. It is possible to produce the cables according to the technology by using low cost non-coherent fibre bundles of fibre optic cables, which also serves to homogenizing the light beam. As it is possible to make the fusing by heat and pressure, it is not necessary to use cohesive agents between the fibres, which cohesive agents would degrade the transmittance of the optical interface.

The technology has several applications. It is possible to provide optic interfaces between optic cables and monochromators with small losses in light intensity. It is also possible to use the active surface of the cable end as a slit for the monochromator thus making a slit-formed aperture unnecessary.

In optical measurement instruments it is also possible to provide a more efficient optical interface when the shape of the illuminating pattern of the light source is other than circular. It is also possible to acquire emission light from chemical samples more efficiently when the sample wells have other than circular form, such as rectangular form. The technology has also uses in optical arrangements including choppers. With a fibre optic cable according to the technology it is possible to produce and receive a light beam, which has a narrow width in relation to its height. Such a light beam can be chopped with narrow apertures, whereby higher chopping frequencies and/or better chopper transmission pulse forms are achieved.

The present technology has also applications in laser technologies. For example, in laser treatment of objects, such as laser machining or laser surgical operations, it is possible to achieve a laser beam which has a rectangular cross section. When such a beam is moved on the surface of an object under treatment, a homogeneous laser treatment can be achieved within the whole treated area.

Exemplary embodiments of fibre optic cables according to the technology are described referring to FIGS. 1, 2a, 2b, 3a-3d, 6a-6b and 8. Then, referring to FIGS. 4, 5, 7 and 8 examples are described on using fibre optic cables according to the technology in optical measurement instruments. Finally, two exemplary methods according to the technology for producing a fibre optic cable are described referring to FIGS. 9 and 10.

Figure 1:
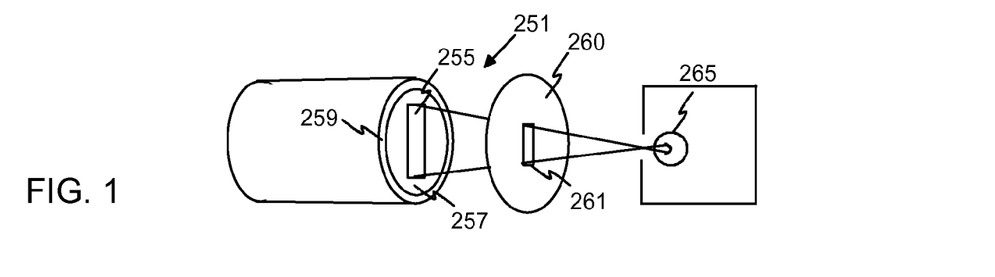
FIG. 1 illustrates a fused first end of an exemplary fibre optic cable according to the technology.

FIG. 1 describes a first end 251 of a first exemplary embodiment of a fibre optic cable according to the technology. The fibre bundle of the cable is fused at the first end, and the bundle has a circular cross section. The fused end of the fibre optic cable is covered at its longitudinal surface with a sleeve 259.

An active surface 255 has been determined for the first end of the fibre optic cable. The active surface has a rectangular form in this example. Thus a part of the fibre ends are located within the active surface, 255, and another part of the fibre ends are located outside the active surface, 257.

When a fibre optic cable is produced according to this exemplary embodiment, the active surface 255 is illuminated with a light source 265. There is a mask 260 with an aperture 261 between the light source and the first cable end for providing a pattern of light at the cable end, which equals to the determined active surface. The aperture has thus the same form as the determined active surface. The mask can be located at any location between the light source and the cable end. However, a location near to the cable end is useful in order to have a high contrast of the illumination at the edges of the active surface. Thus it is useful to have the mask in contact with the end of the cable end. However, in FIG. 1 the mask is shown at a distance from the cable end in order to clarify the illustration.

Figure 2A:
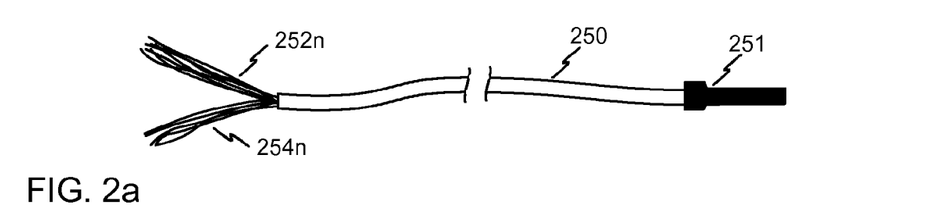
FIG. 2a illustrates an exemplary fibre optic cable according to the technology with second ends of fibres separated into two groups.

During the illumination, the optic fibres of the second end of a cable 250 are separated into two groups 252n and 254n as shown in FIG. 2a. The separation is made on the basis of the illumination received at the end of each fibre. The fibres of group 252n have their first ends within the active surface, and the second ends of these fibres therefore receive illumination from the light source 265. The fibres with illuminated second ends thus form the first group of fibres 252n. The fibres of the second group 254n have their first ends outside the active surface and they are therefore not illuminated by the light source 265.

Figure 2B:
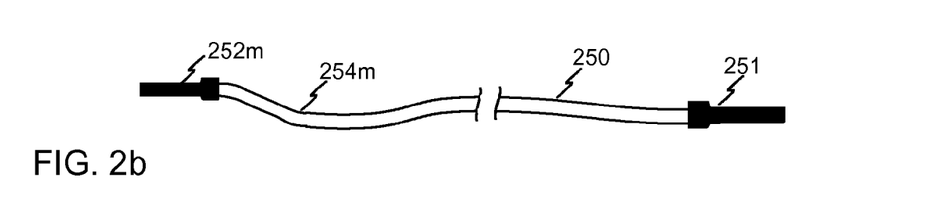
FIG. 2b illustrates an exemplary fibre optic cable according to the technology in a final form.

FIG. 2b shows an exemplary finished cable according to the technology. The ends of the first group of fibres 252n are fused and covered at their longitudinal surfaces with a sleeve. This fused end of circular cross section thus forms a second optical interface 252m of the cable 250. The ends of the second group of fibres 254n are cut, 254m. So in this case the fibres outside the active surface are not used. However, it is also possible to provide a cable wherein the second fibre ends at the second group of fibres are also fused and thus form a third optical interface of the cable. In this case the first end of the cable has two active surfaces.

The exemplary fibre optic cable illustrated in FIGS. 1, 2a and 2b is produced by using a mask which has an aperture.

However, it is alternatively also possible to use other kind of masks which provide a different illumination at the active surface compared to the illumination outside the active surface. For example, the mask may be made of two optical filter materials, wherein the mask provides illumination of different colours at the active surface compared to the area outside the active surface. The separation of the fibres at the second end of the cable can then be made based on the colour of illumination at each fibre end. It is naturally also possible to use other kind of filtering than colour filters. Further, it is possible use a mask which prevents the illumination of the active surface and provides illumination to the surface outside the active surface. In this case, such second fibre ends which are not illuminated are separated into a first group of fibres which are fused and used as a second optical interface of the cable. The essential principle therefore is that the mask has a different transmission characteristic for light beams that enter a determined active surface compared to the transmission characteristic for the light beams which enter the area outside said active surface of the first cable end. The different transmission characteristic may mean, for example, different transmission coefficient for all wavelengths of light, or it may mean different transmission coefficient for different wavelengths of light. The mask may thus have filters of different colours for each area, and the fibres can be separated on the basis of the colour of light emitted at the second end of each fibre, as was mentioned above.

The fibre ends of the first end of the cable can alternatively be illuminated by applying light to the second end of the cable. In this case, a reflecting mask is applied at the first end of the cable. The mask has a different reflection characteristic at the determined active surface compared to the area outside the determined active surface. For example, the mask may be a mirror of a shape and size of the determined active surface. In this case, the fibres which have their first end within the active surface receive reflected illumination, while the first fibre ends outside of the determined active surface do not receive reflected illumination. Thus the fibres can be separated into two groups on the basis of whether a fibre end is illuminated by reflected light or not.

Figure 3A:
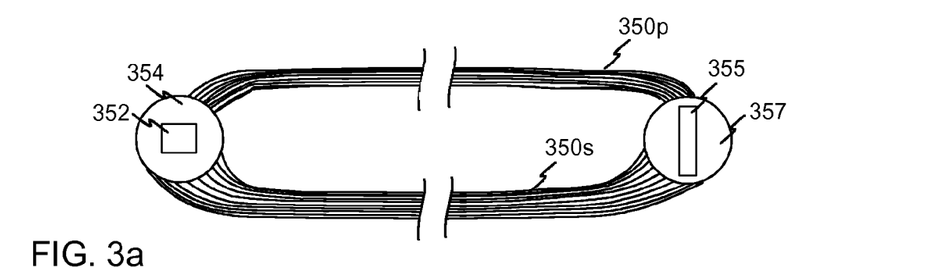
FIG. 3a illustrates a second exemplary fibre optic cable according to the technology which is made of separate fibre bundles.
Figure 3B:
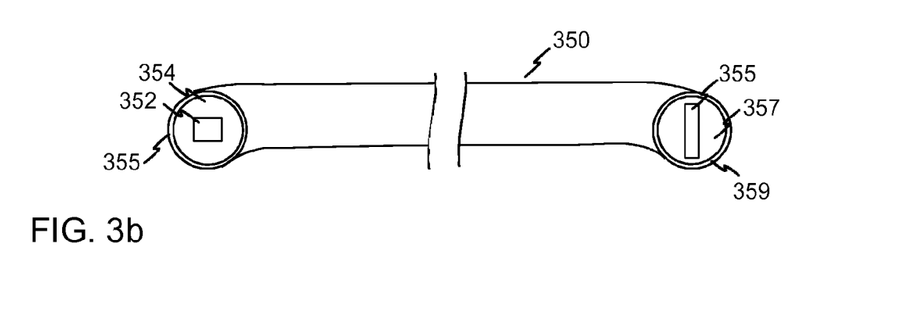
FIG. 3b illustrates a second exemplary fibre optic cable according to the technology in a completed form.

FIGS. 3a and 3b describe a fibre optic cable according to a second embodiment of the technology, wherein the cable is formed of two fibre bundles 350p and 350s, and both ends of the cable have an active surface of a determined pattern. FIG. 3a illustrates a semi-finished optical cable including a first fibre bundle 350p which has its fibre ends within the active surfaces, and a second bundle 350s which has its fibre ends outside the active surfaces. The first end of the cable has a rectangular active surface 355, which has much smaller width than height. The fibre ends 357 of the second fibre bundle are used for surrounding the active surface in order to form a circular outline for the cable end.

The second end of the cable has a square active surface 352 comprising the second fibre ends of the first fibre bundle 350p. The second fibre ends 354 of the second fibre bundle are used for surrounding the active surface in order to form a circular outline for the second end of the cable.

FIG. 3b illustrates the fibre optic cable when it is completed. The both ends of the cables are fused, and the two fibre bundles have been incorporated within a sleeve 359, which covers the cable along its whole length.

Figure 3C:
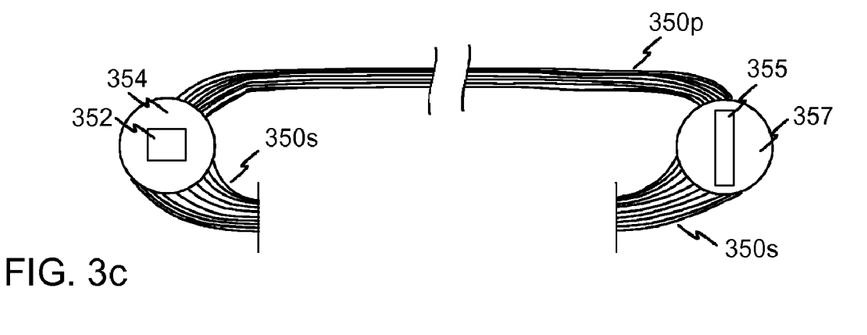
FIG. 3c illustrates a further exemplary fibre optic cable according to the technology which is made of separate fibre bundles.
Figure 3D:
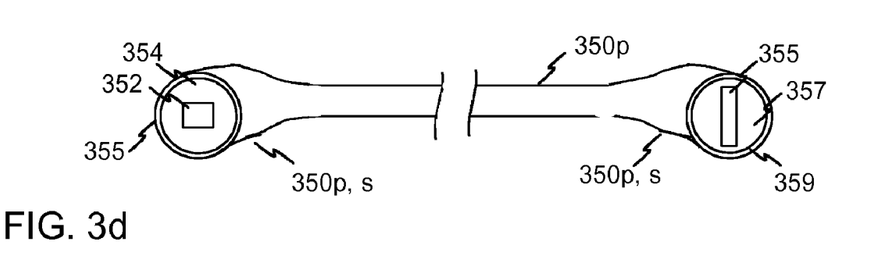
FIG. 3d illustrates a second exemplary fibre optic cable according to the technology in a completed form.

If the second fibre bundle is not used for guiding light, it is possible to use only short pieces of second bundles at the ends of the cable as auxiliary bundles, and not to convey the second bundle all the way between the cable ends. FIGS. 3c and 3d illustrate such a cable where the second bundle 350s is just a short bundle at both ends of the cable. It is possible to use a second fibre bundle of FIG. 3a and cut away the middle part of the bundle, or to use initially short auxiliary fibre bundles at the both ends of the cable. In a completed cable of FIG. 3d the second fibre bundles are covered with a sleeve. Only the first bundle 350p is conveyed between the ends of the cable and the cable of FIG. 3d thus has a much smaller width compared to the cable of FIG. 3b. Further, the second bundle may be made of fibres which are of other material than the first bundle. If the second bundle is not used for transferring light it is possible use some low-cost fibres which do not necessarily conduct light but which have similar mechanical and thermal characteristics as the fibres of the first bundle, and which are not fluorescent.

Figure 4:
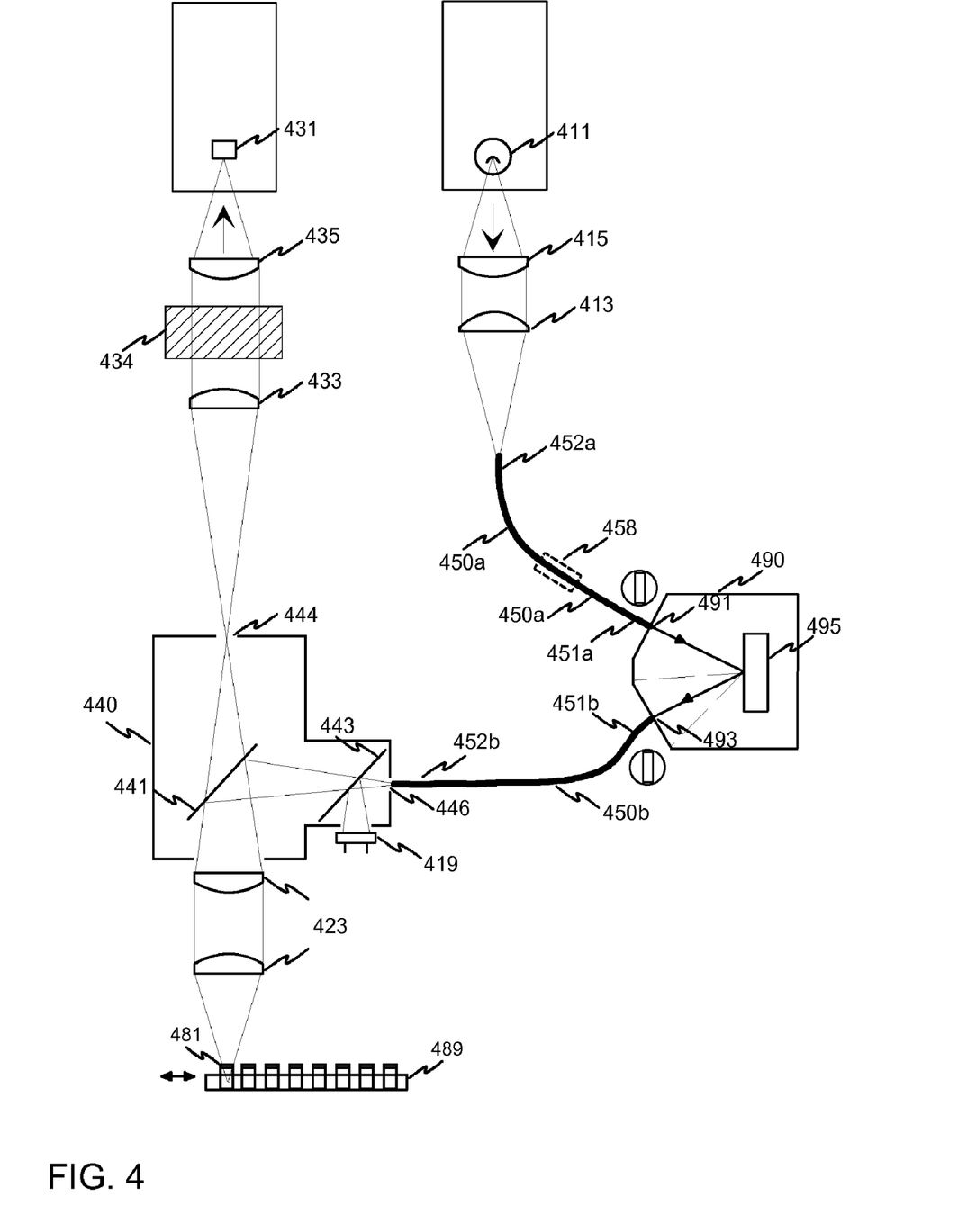
FIG. 4 illustrates an exemplary optical arrangement of a measurement instrument where a fibre optic cable according to the technology and a monochromator is utilised.

FIG. 4 illustrates main components and optical paths of an exemplary optical analyser instrument according to the technology. The instrument has an illumination source 411 for the excitation of a sample. The light beam from the light source is focused with lenses 415 and 413 to an end 452a of a fibre optic cable 450a. The light beam is guided with the cable to a slit aperture 491 of a monochromator 490. The fibre optic cable 450a is a cable according to the technology, and the end 451a of the cable is in this case a first end of the cable. The active area of fibre ends has a rectangular pattern with the form equal to the slit 491 of the monochromator. Thus it is possible to achieve an optic interface with small attenuation of light. It is also possible to connect the cable end through an aperture of the monochromator which has a dimension of the cable diameter. Thus the active surface of the cable end may serve as the input slit, and it is not necessary to provide a narrow input slit in the monochromator wall.

The second end 452a of the cable 450a may be a fused end with a circular active area. However, if the emitting surface of the light source has some other form than circular, it may be useful to have the same form in the active surface of the fibre optic cable as well. If other than circular form of the active surface is required in both ends of the cable 450a, it is useful to use a cable according to the second embodiment of the technology described above. Another alternative is to combine two cables according to the first embodiment of the technology described above. The two cables can be combined with an optic connector 458, which connects the second ends of both cables, which ends have a circular active area of same size. In this case, the first end 451a of one of the cables is coupled to the monochromator, and the first end 452a of another cable is coupled to the light source. By using active surfaces of determined patterns at active surfaces of both ends of the cable or the combined cable it is possible to provide suitable optical interfaces for both the light source and the monochromator.

The monochromator 490 has a dispersive component 495, such as a grating or a prism. The light beam is directed from the slit 491 to the dispersive component 495, and there may be other optical components (not shown in Figure), such as lenses between the slit and the dispersive component. The dispersive component reflects the light beam so that the reflection angle is dependent on the wavelength of the light component. The dispersive component thus disperses the light into components with different reflection angles. The monochromator has an output slit 493 which transmits components of light with a desired band of wavelengths.

The output light beam from the monochromator is directed to an end 451b of a fibre optic cable 450b. The end 451b is a first end of a fibre optic cable according to the technology, and the active surface area of the cable end has a form of the output slit 493 of the monochromator. It is also possible to connect the cable end through an aperture which has a dimension of the cable diameter. Thus the active surface of the cable end may serve as the output slit, and it is not necessary to provide a narrow output slit in the monochromator wall.

The second end 452b of the fibre optic cable 450b is coupled to an aperture 446 of an optical module 440. The second end of the optical fibre may have a circular active surface or, if necessary, some other form of the active cable end can be provided also at the interface to the optical module. If the sample wells have a rectangular shape, it may be useful to have an active surface of the cable end having a rectangular or near rectangular form.

Within the optical module 440, the excitation light beam is reflected by a dichroic mirror 441. The excitation beam is further directed into the sample 481 through an opening at the bottom of the optical module and a lens system 423. A part of the illumination light is reflected by a beam splitter mirror 443 and guided through an aperture into a reference detector 419 in order to give reference information on the actual illumination intensity. This way high feedback accuracy is achieved. A beam splitter mirror can be provided with an uncoated disc of quartz, which transmits and reflects a light beam in a predetermined proportion. It is also possible to form a reflective coating on a transparent disc in form of e.g. stripes or dots, which cover only a part of the mirror surface.

The emission beam from the sample 481 is directed with the lens system 423 through an opening into the optical module 440, where it passes the dichroic mirror 441. The dichroic mirror can be designed for each label so that it reflects excitation wavelength but transmits emission wavelengths. The emission beam is then focused through an aperture 444 and collimated with a lens 433. The emission beam is further directed through an interference filter 434 in order to prevent light with a wavelength outside the emission from passing to the detector. The emission beam is then focused with lens 435 to the detector 431. The detector 431 is a photon multiplier tube (PMT), but alternatively other types of detectors can also be used, such as a photo diode detector. The signal received from the detector is then amplified and processed to achieve a value for the intensity of the emission. These excitation and emission parts of the instrument can be used, except for photoluminescence measurements, also for e.g. photometric and chemiluminescence measurements.

The optical measurement instrument of FIG. 4 further includes a sample platform, which has means for moving a sample tray 489 in order to position successive samples 481 into the measurement locations. The optical components of FIG. 4 are a part of a top measurement head (not shown entirely in the Figure), which includes components for providing an excitation beam and for detecting emissions from above the sample. The instrument may also have a bottom measurement head, which includes components for providing an excitation beam and/or for detecting emissions from below the sample.

Figure 5:
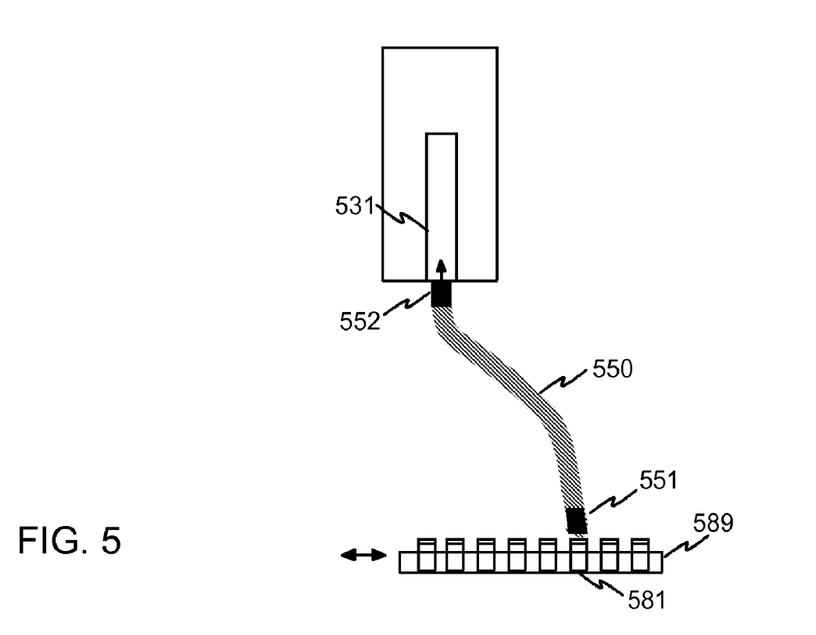
FIG. 5 illustrates an exemplary optical arrangement of a measurement instrument where an optical cable according to the technology is used for chemiluminescence measurements.

FIG. 5 illustrates an arrangement for measuring chemiluminescence wherein fibre optic cable according to the technology is used. The arrangement includes a movable sample tray 589 including sample wells 581. A chemical reaction within the samples causes emission radiation which is received with a fibre optic cable 550. In order to acquire the emission with high efficiency, it is useful that the active end 551 of the fibre optic cable has an active surface which is of the same form and size as the top surface of the sample. The sample wells are commonly rectangular, in which case the end 551 of the fibre optic cable has an active surface with a same rectangular form as the sample well. This can be achieved using a fibre optic cable according to the technology wherein the first end 551 is located above the sample to be measured. The second end 552 of the cable 550 is coupled to a detector 531, and the second end of the fibre optic cable has a circular active surface.

With an arrangement according to FIG. 5 it is possible to achieve a high acquisition efficiency of the emission radiation, which improves the accuracy of chemiluminescence measurements and/or increases the amount of samples that can be measured in a given time.

Figures 6A, 6B:
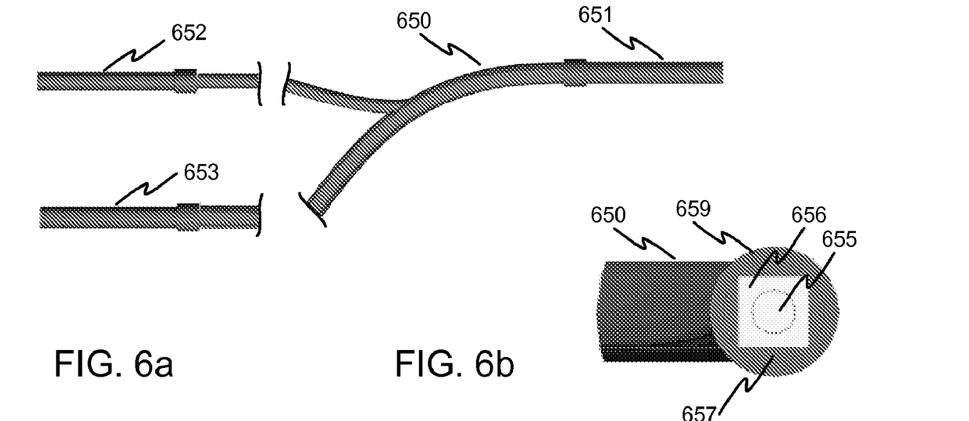
FIG. 6a illustrates an exemplary fibre optic cable according to the technology, in which the cable end has two active patterns.
FIG. 6b illustrates an exemplary end of a fibre optic cable according to the technology, in which the end has two active patterns.

FIGS. 6a and 6b illustrate an exemplary fibre optic cable 650 according to the technology wherein the first end 651 of the cable has two active surfaces 655, 656. FIG. 6a illustrates a side view of the cable, and the FIG. 6b illustrates an enlarged view of the first end of the cable. The first active surface 655 is of a circular shape and the second active surface 656 has a square form around the first active surface 655. There are unused fibres 657 outside the second active surface 656. The cable end also has a sleeve 659.

When the exemplary cable of FIGS. 6a and 6b has been produced according to a first exemplary embodiment of the technology, the active surfaces have been illuminated for separating the fibres at the second end of the cable. For example, this may have be done in two phases where the first active surface is first illuminated, and the illuminated fibre ends at the second end of the cable are separated and fused to form a second optical interface 652. Then, the second active surface (and possibly also first active surface) is illuminated, and the illuminated remaining fibre ends at the second end of the cable are separated to form a third optical interface 653. The remaining fibres (not shown in Figure) at the second end of the cable can then be cut if they are not to be used. Alternatively the first end of the cable can be illuminated using e.g. different colour filtering for illuminating the first active surface compared to illuminating the second active surface. This way it is possible to separate all fibres at the second end of the cable simultaneously based on the colour of possible illumination at each fibre end.

When the exemplary cable of FIGS. 6a and 6b has been produced according to a second exemplary embodiment of the technology, three bundles of fibres have been provided. The fibre ends of the first bundle have been used for forming the first active surface for the first cable end. The fibre ends of the second bundle have then been used for forming the second active surface for the first cable end. The fibre ends of the third bundle are used to complement the cable end into a circular outline, after which the cable end has been fused. At the second end of the cable it is possible to provide separate optical interfaces by fusing separately the fibre ends of the first bundle and the fibre ends of the second bundle. Alternatively, it is possible to provide a single optical interface with determined active surfaces in a same manner as producing the optical interface at the first end of the cable.

Figure 7:
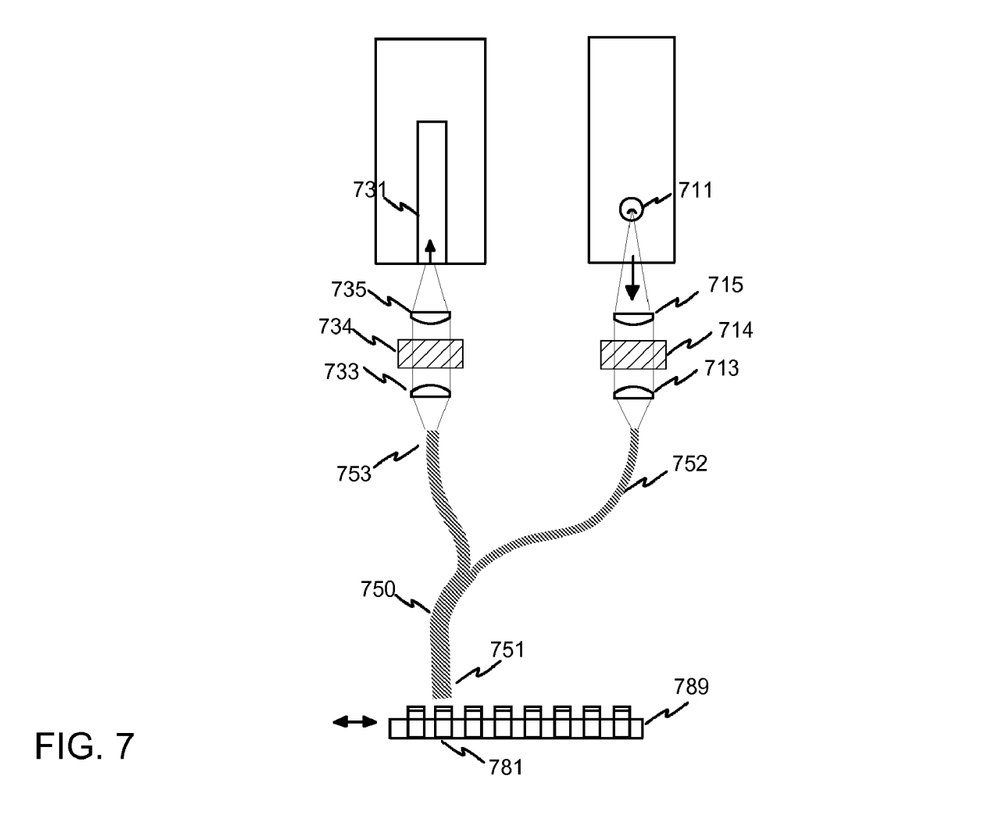
FIG. 7 illustrates an exemplary optical arrangement of a measurement instrument where an optical cable according to the technology is used for photoluminescence measurements.

FIG. 7 illustrates an arrangement of optical components of an exemplary optical instrument for measuring photoluminescence of samples. A fibre optic cable according to FIGS. 6a and 6b can be used in this arrangement. The arrangement includes a movable sample tray 789 with sample wells 781 of square or other rectangular shape. A fibre optic cable 750 according to the technology is used for both excitation and detection of the sample. The first end of the cable has two active surfaces according to FIG. 6b. The inner, first active surface has in this embodiment a circular form. The fibres of the first active surface are led to a second optical interface 752 of the cable. The second optical interface 752 is coupled to receive illumination from a light source 711. The light received from the light source is collimated with a lens 715 for an excitation filter 714, and the filtered light is further focused with a lens 713 to the second optical interface 752 of the cable. The sample is thus excited with an excitation light which is provided by the light source, filtered and guided to the sample with the fibre optic cable. Instead of an optical filter 714, it is also possible to use e.g. a monochromator according to FIG. 4.

The second active surface of the first cable end 751 is used for receiving emission from the sample. The fibres of the second active surface are led to a third optical interface 753 of the cable 750. The light received from the third optical interface 753 is collimated with a lens 733 for an emission filter 734, and the filtered emission beam is further focused with a lens 735 to the sensitive area of a detector 731.

The arrangement of FIG. 7 provides simple means for photoluminescence measurements with high optical efficiency.

Figure 8:
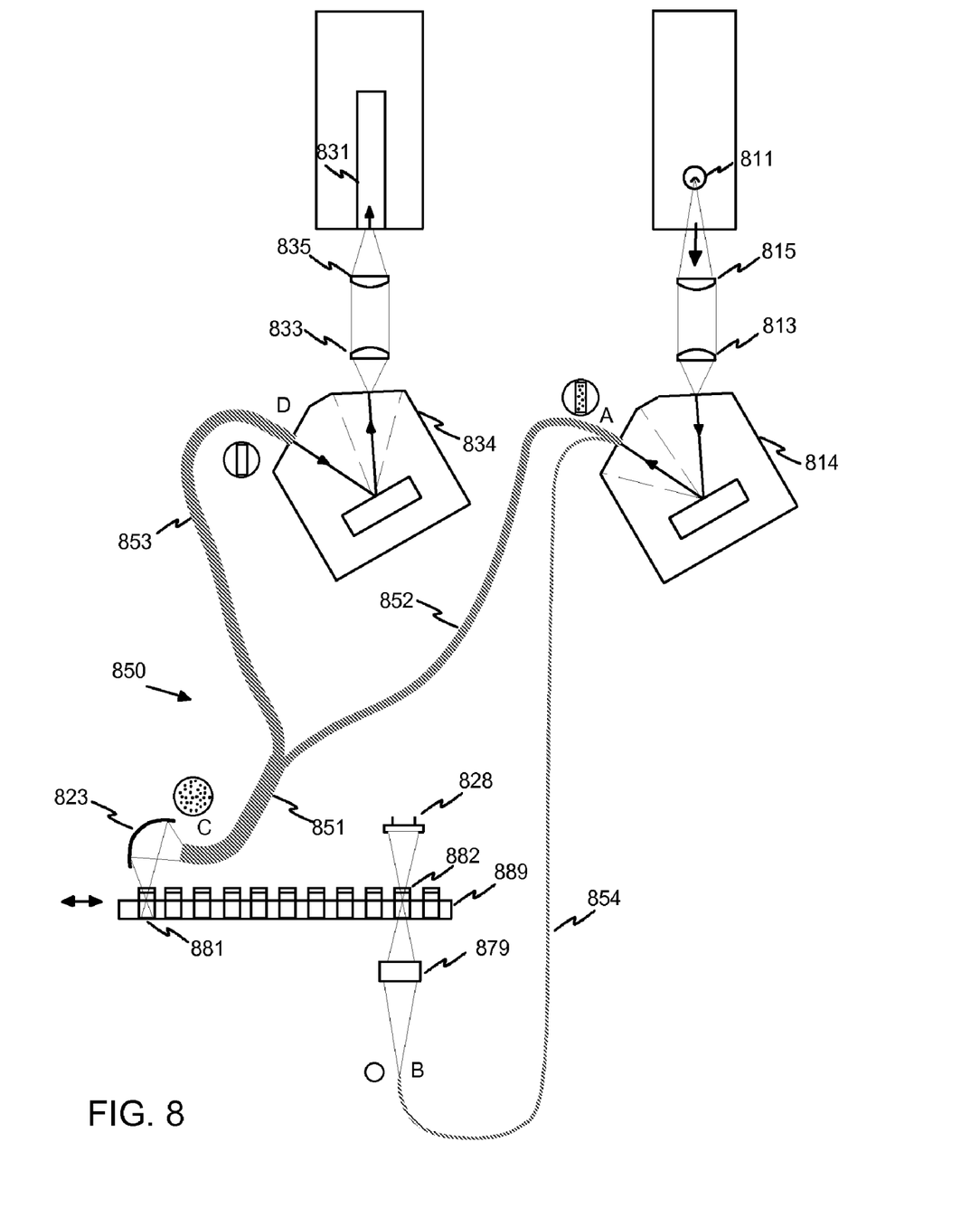
FIG. 8 illustrates an exemplary optical arrangement of a measurement instrument where a branched optical cable according to the technology is used for photoluminescence, chemiluminescence and photometric measurements.

FIG. 8 illustrates an arrangement of optical components of a further exemplary optical instrument for providing photoluminescence, photometric and possibly chemiluminescence measurements of samples. Also in this example there is a single cable with several branches for guiding both illumination light from the light source and the emission light from a sample. Illumination from a light source 811 is focused with lenses 815 and 813 into an input slit of a monochromator 814. One end A of a fibre optic cable 850 is coupled to the output of the monochromator. The active surface of the fused cable end A has a rectangular form of a narrow slit. The forms of the active surfaces are shown in the Figure. The active surface at the end A includes fibre ends from two fibre bundles 852 and 854. The ends of the bundles 852 and 854 are mixed within the active surface in order to achieve a homogeneous illumination for both bundles.

The fibre bundle 852 provides excitation light for photoluminescence measurements and the bundle 852 provides illumination for photometric measurements. The intensity of light required for photometric measurement is generally much smaller than the intensity of light required for photometric measurements. Therefore the active surface at end A can have a much larger number of fibre ends from the bundle 852 then from bundle 854. The relation may be e.g. 90%:10% respectively. The end B of the bundle 852 is a fused end with a circular active surface. The light beam from the end B is focused to a sample 882 at a sample tray 889 with a set of optical components 879. After being transmitted through the sample, the light beam is measured with e.g. a photodiode detector 828. Since the same illumination source and monochromator provides illumination for both photoluminescence measurements and photometric measurements, it is usually not possible to make the two types of measurements simultaneously. In an arrangement of FIG. 8 the sample locations for the photoluminescence measurements and the photometric measurements are both illuminated when either of the measurements is made. However, this does have any negative effect on the measurements.

The bundle 852 provides excitation illumination for photoluminescence measurement of a sample 881. The active surface of end C of the fibre optic cable 850 includes fibre ends from both bundles 852 and 853. Bundle 853 is used for guiding emission light to a monochromator 834. The fibre ends of the bundles 852 and 853 have been mixed and fused within a same circular surface of the cable end C. The active surfaces of the bundles are thus overlapping. The size of the active surface and the number of fibres required for receiving the emission light is generally larger than active surface and the number of fibres required for providing excitation light to the sample. Therefore the number of fibres is usefully larger in the bundle 853 than in the bundle 852. The proportions of the numbers of fibres may be e.g. 2:1 respectively. The arrangement of FIG. 8 also includes an elliptic mirror 823 for reflecting and focusing the excitation light from the cable end C into the sample and for reflecting and focusing the emission light from the sample into the cable end C. It is also possible to use a lens system instead of the elliptic mirror.

The end D of the bundle 853 is exemplary a fused end which has a circular outline but the active surface has a form of a rectangular slit, which is useful for the optical coupling to the monochromator 834 input. Such a fused end can be made according to the technology by using dummy fibres around the active surface. The beam received from the output slit of the monochromator 834 is focused to the input of a detector 831 with lenses 833 and 835. Instead of lenses, it is possible to use a fibre optic cable according to the technology between the monochromator and the detector, and also between the light source and the monochromator 814. It is also possible to couple the output of the monochromator directly to the input of the detector without any separate optics or optic fibres.

The above description of embodiments for an optical instrument has concerned just optical components and arrangements. An optical measurement instrument is also equipped with electronics for amplifying and processing the signals from the detectors, as well as electronics for driving the light source. There is also control electronics provided for controlling the measurements, such as adjusting the monochromator, selecting an emission filter, selecting an the optical module, controlling the position of the sample tray, and controlling the positions of the measurement head relative to the sample platform. The control of the measuring process in an optical measurement instrument generally takes place in an arrangement of processing capacity in the form of microprocessor(s) and memory in the form of memory circuits. Such arrangements are known as such from the technology of analyzers and related equipment. To convert a earlier known optical instrument into equipment according to the technology it may be necessary, in addition to the hardware modifications, to store into the memory means a set of machine-readable instructions that instruct the microprocessor(s) to perform the operations with suitable parameters. Composing and storing into memory of such instructions involves known technology which is within the capabilities of a person skilled in the art.

Figure 9:
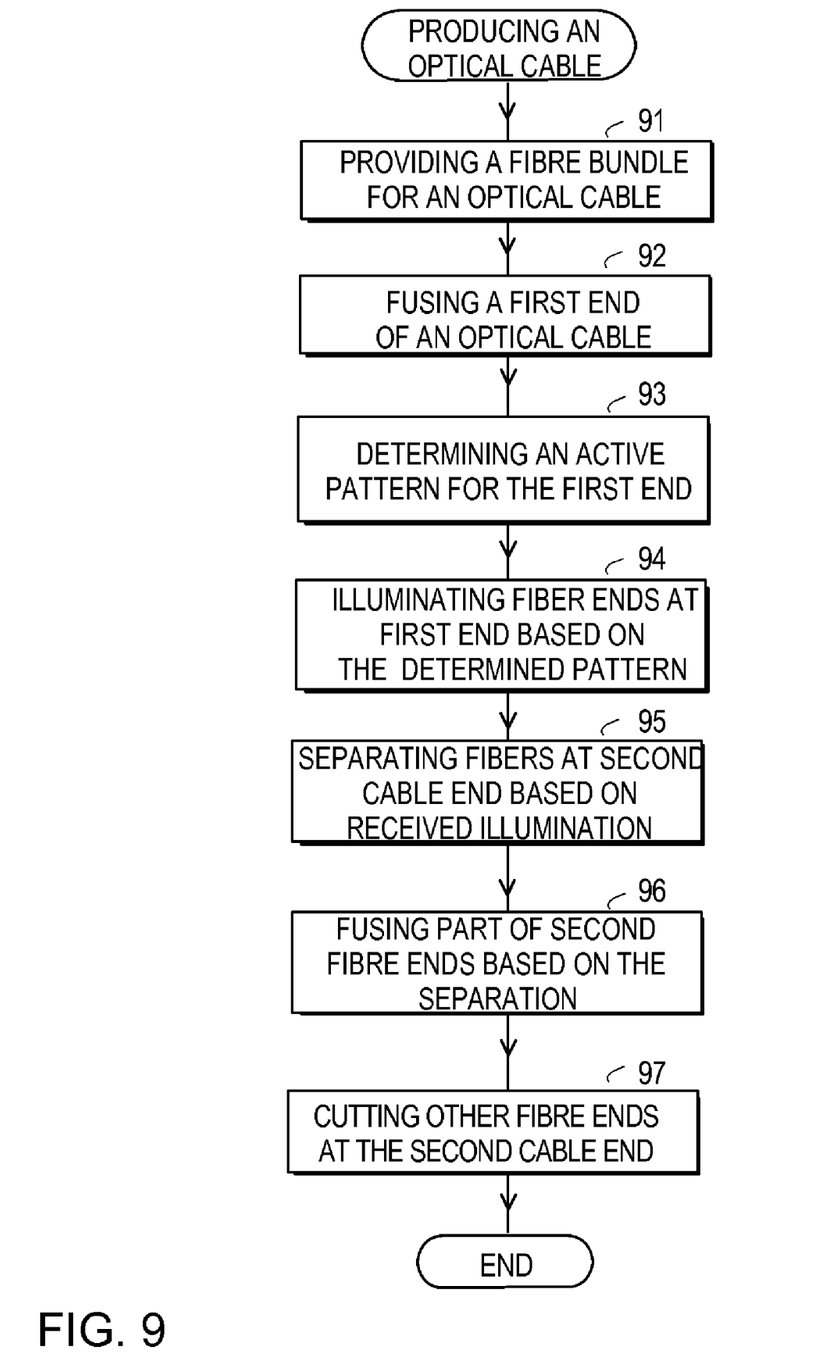
FIG. 9 illustrates a flow diagram of an exemplary method for producing a fibre optic cable according to the technology.

FIG. 9 illustrates a first exemplary embodiment of a method according to the technology for producing a fibre optic cable according to the technology by processing a non-coherent bundle. First, a fibre bundle of a suitable length is provided in phase 91. At the first end of the cable, the bare fibre bundle is fused by providing radial pressure to the fibres and heating in phase 92. Thus the gaps between fibres are removed, and the cross section of the cable becomes/remains circular. Next in phase 93, a pattern is determined for the active surface of the first end of the cable, a rectangular form for example. Then the first end of the cable is illuminated on the basis of the determined pattern in phase 94. Such an illumination can be achieved, for example, by using a mask which has an aperture of the form and size of the determined active surface. The mask is placed between an illumination source and the cable end so that an area according to the determined pattern is illuminated at the surface of the fused cable end. As described above referring to FIG. 1, it is also possible to use masks with optic filter materials, and it is possible to use reflecting masks if the first cable end is illuminated by applying light to the second end of the cable.

While illuminating the first end of the cable according to the determined pattern, fibres of the second end are separated into at least two groups, phase 95. The separation is made on the basis of the illumination detected at each fibre end. For example, fibres with illuminated ends are separated into a first group, and fibres with no illumination at their ends are grouped into a second group. One bundle of separated fibres is then fused to have a circular cross section, phase 96. For example, if rectangular area is illuminated at the first cable end as a desired active surface, the group of fibres with illuminated second ends is exemplary fused at the second cable end. The fibres of the remaining group(s) may be fused to form further ends of the cable, or they can be cut if they are not needed, phase 97. However, it is also possible to provide the optical interface(s) at the second cable end without fusing the fibre ends. It is possible to provide a sleeve around the cable at its entire at the final stage, or it is possible to provide a sleeve at the middle part of the cable before processing the cable ends, and to provide separate pieces of sleeves at the cable ends after processing the ends.

Figure 10:
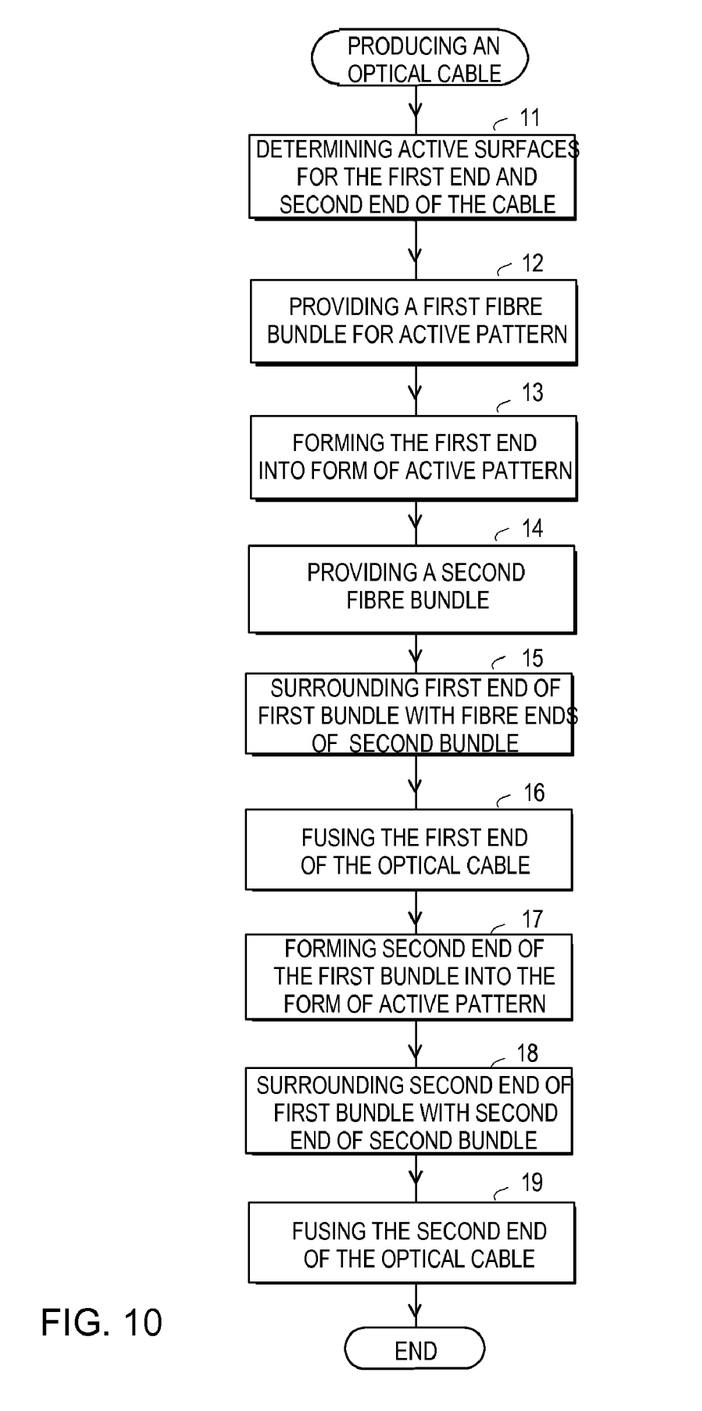
FIG. 10 illustrates a flow diagram of another exemplary method for producing a fibre optic cable according to the technology.

FIG. 10 illustrates a second exemplary method according to the technology for producing a fibre optic cable according to the technology. In this method the fibre optic cable is produced using bundles of fibres. With this method it is possible to produce a fibre optic cable, which has a determined active surface in both of its ends.

First in phase 11 the active surfaces are determined for the first and second ends of the fibre optic cable. The pattern of the active surface includes its form and size. In this example, we can assume that the form of the active surface in the first cable end is rectangular. Next in phase 12 a first fibre bundle is provided for the active surface of the first end. The number and diameter of fibres in the bundle should be such that the fibre ends of the bundle will form the active surface of the right size and form after the fibre ends will be fused. The first ends of the first bundle are then set into the right form of the determined active surface, phase 13. It is possible to use a use a jig which has an opening of the right form in order to make and keep the fibre ends of the first bundle in the right form.

Next in phase 14 a second fibre bundle is provided. In phase 15 the first fibre ends of the second fibre bundle are set around the first fibre ends of the first bundle in such a way that the first ends of the fibres form a circular outline. The first ends of fibres are set into a cylindrical fusing head of a fusing apparatus. The jig which keeps the first active fibres in a correct form is then removed, and the fibre ends of the first and second bundles are fused in phase 16 into an integrated fused end of the fibre optic cable. Heat and radial pressure are applied in fusing in order to remove the interspaces between adjacent fibre ends. The fused end now includes the first optical interface of the fibre optic cable. It should be noted that the optic fibres of a cable usually have a cladding which is made of material with lower refractive index than the core of the fibre. The purpose of the cladding is to enable total reflection at the interface between the fibre core and the cladding. While the cladding is a part of a fibre, it is not the purpose of the fusing to remove the cladding and the cladding is thus not an interspace between the fibres.

After processing of the first end of the fibre optic cable the second end of the fibre optic cable is processed. In this example, we can assume that the form of the active surface in the second cable end is square. In phase 17 the second ends of the first bundle are then set into the right form of the determined active surface, phase. Again, it is possible to use a use a jig which has an opening of the right form in order to make and keep the second fibre ends of the first bundle in the right form. Next in phase 18 the second fibre ends of the second fibre bundle are set around the second fibre ends of the first bundle in such a way that the second ends of the fibres form a circular outline. The fibre ends are set into a cylindrical fusing head of a fusing apparatus. The jig which keeps the first active fibres in a correct form is then removed, and the fibre ends of the first and second bundles are fused in phase 19 into an integrated fused end of the fibre optic cable. The second fused end now includes the second optical interface of the fibre optic cable. However, it is also possible to provide the second optical interface without fusing.

It should be noted, that if the second bundle is not used for transferring light, it is not necessary to lead the second bundle all the way between the ends of the cable. It is thus possible to cut away the middle part of the second bundle after the ends have been fused. Alternatively it is possible to use just short second bundles at each end of the cable. It should also be noted that the second bundle may be made of fibres which are of other material than the first bundle. If the second bundle is not used for transferring light it is possible use some low-cost fibres which do not necessarily conduct light but which have similar mechanical and thermal characteristics as the fibres of the first bundle, and which are not fluorescent.

The example of FIG. 10 related to producing a fibre optic cable where both ends have a determined active surface which can have any determined pattern. However, it is naturally possible to use the method according to FIG. 10 also for producing a cable where only one end has a predetermined active surface of other than circular form. It is, for example, possible to fuse the second ends of the first fibre bundle into a circular fused end without including any fibres from the second fibre bundle into this fused end. The second ends of the second fibre bundle can be cut, or fused into a further circular end providing a third optical interface of the cable.

The exemplary methods described above related to cable ends where an active surface is an inner surface of the cable end. However, it is naturally possible that the active surface also other form, such as a form of a ring, wherein there are other fibre ends in the middle of the ring but are not included in the active surface. In this case, if a method of FIG. 10 is used, fibre ends of a second fibre bundle must first be set to form the inner circle of the ring. The first ends of the first fibre bundle are then set to surround the fibre ends forming the inner circle. Further first ends of the second fibre bundle (or of a third fibre bundle) are then set to surround the first ends of the first fibre bundle in order to form a circular outline for the first end of the cable.

In this patent specification the structure of the components in an optical measurement instrument is not described in more detail as they can be implemented using the description above and the general knowledge of a person skilled in the art.

Above, only some embodiments of the solution according to the technology have been described. The principle according to the technology can naturally be modified within the frame of the scope defined by the claims, for example, by modification of the details of the implementation and ranges of use.

For example, the above embodiments have related to a rectangular active surface area of the first end of the cable. However, the determined active surface can be of various alternative shapes and sizes. Therefore, even if a rectangular shape is useful in many applications, the technology is not in any way restricted to such shapes.

The described embodiments have included 1-2 active surfaces and 1-2 optical interfaces at each cable end, and 2-3 bundles of fibres in the cable. However, the number of active surfaces, optical interfaces and fibre bundles can naturally be higher than described in the examples.

It has also been mentioned that the cable ends are fused to have a circular cross section. Although this is a useful manner of fusing, it should be understood that fusing can alternatively be made into other forms than exactly circular one.

Although it is useful to use a non-coherent fibre optic cable, a fibre optic cable according to the technology can also be made with a cable where the order of the fibres is coherent along the cable.

Further, the fibre optic cable has been described to have a sleeve along the whole length of the cable, but it is possible to produce a cable according to the technology even without any sleeve or with a partially covering sleeve.

Although the technology is described with an arrangement where the light source and the detector are located on a top measurement head locating above the sample, it is also possible to install them on a bottom measurement head located below the sample. It is also possible to use illumination from above and detection from below the sample or vice versa.

Also, although the technology has been described with reference to microtitration plates of rectangular shape it is equally applicable to any form of sample matrixes or single sample wells.

The invention claimed is:

1. A fibre optic cable including a plurality of optic fibres, wherein:
   the fibre optic cable has a first cable end and a second cable end,
   each optic fibre has a first fibre end and a second fibre end,
   the fibre optic cable has a first optical interface at the first cable end and a second optical interface at the second cable end,
   at least part of the optic fibres have a non-coherent mutual arrangement between the first and second cable ends,
   at the first cable end, a ratio of a cross sectional area of the first fibre ends to a cross-sectional area of spaces between the individual optic fibres has been increased by fusing at least part of the first fibre ends, the fused first fibre ends forming at least part of the first optical interface,
   the first optical interface has a determined first active surface area consisting of an integral piece of area and including the first fibre ends of a first group of optic fibres, each optic fibre whose first fibre end is located inside said first active surface area belonging to the first group of optic fibres,
   the second optical interface has a determined second active surface area consisting of an integral piece of area and including the second fibre ends of the first group of optic fibres, each optic fibre whose second fibre end is located inside said second active surface area belonging to the first group of optic fibres, and
   at the first cable end, the first fibre ends of a second group of optic fibres are located between the first active surface and an outline of the first cable end.

2. The fibre optic cable according to claim 1, wherein the determined first active surface area is noncircular.

3. The fibre optic cable according to claim 1, wherein one or both of the determined first active surface area and the determined second active surface area has/have a rectangular shape.

4. The fibre optic cable according to claim 1, wherein a transversal outline of all the first fibre ends is circular at the first cable end.

5. The fibre optic cable according to claim 1, wherein the optic fibres belonging to the second group of optic fibres are shorter at the second cable end than the optic fibres belonging to the first group of optic fibres.

6. The fibre optic cable according to claim 1, wherein the first group of optic fibres and the second group of optic fibres are both separate fibre bundles.

7. The fibre optic cable according to claim 1, wherein the first optical interface has a determined third active surface area consisting of an integral piece of area and including the first fibre ends of a third group of optic fibres, each optic fibre whose first fibre end is located inside said third active surface belonging to the third group of optic fibres, and the second fibre ends of the third group of optic fibres are arranged to form a third optical interface of the fibre optic cable.

8. The fibre optic cable according to claim 1, wherein the fused fibre ends are heat treated and/or pressure treated.

9. The fibre optic cable according to claim 1, wherein the fibres of the first group of optic fibres have a non-coherent mutual arrangement between the first and second fibre ends of the first group of optic fibres.

10. The fibre optic cable according to claim 1, wherein at least part of the second fibre ends of the fibres of the second group of optic fibres are adjacent to the second fibre ends of the fibres of the first group of optic fibres, the second cable end being an integral cable end formed by the second fibre ends of the fibres of both the first and second groups of optic fibres.

11. The fibre optic cable according to claim 1, wherein the fibre optic cable has two branches which both have first ends, first optical interfaces, and first groups of optic fibres, wherein the second ends of the two first groups of optic fibres are connected to form a second end and at least one second optical interface of the fibre optic cable.

12. An optical measurement instrument for measuring samples, the optical measurement instrument comprising a fibre optic cable including a plurality of optic fibres, wherein:
the fibre optic cable has a first cable end and a second cable end,
each optic fibre has a first fibre end and a second fibre end,
the fibre optic cable has a first optical interface at the first cable end and a second optical interface at the second cable end,
at least part of the optic fibres have a non-coherent mutual arrangement between the first and second cable ends,
at the first cable end, a ratio of a cross sectional area of the first fibre ends to a cross-sectional area of spaces between the individual optic fibres has been increased by fusing at least part of the first fibre ends, the fused first fibre ends forming at least part of the first optical interface,
the first optical interface has a determined first active surface area consisting of an integral piece of area and including the first fibre ends of a first group of optic fibres, each optic fibre whose first fibre end is located inside said first active surface area belonging to the first group of optic fibres,
the second optical interface has a determined second active surface area consisting of an integral piece of area and including the second fibre ends of the first group of optic fibres, each optic fibre whose second fibre end is located inside said second active surface area belonging to the first group of optic fibres, and
at the first cable end, the first fibre ends of a second group of optic fibres are located between the first active surface and an outline of the first cable end.

13. The optical measurement instrument according to claim 12, wherein the instrument comprises means for performing photoluminescence measurement, chemiluminescence measurement and/or photometric measurement of samples.

14. A method for producing a fibre optic cable that includes a plurality of optic fibres, each optic fibre having a first fibre end and a second fibre end and the fibre optic cable having a first optical interface at a first cable end and a second optical interface at a second cable end, the method comprising:
increasing, at the first cable end, a ratio of a cross-sectional area of the first fibre ends to a cross-sectional area of spaces between the individual optic fibres by fusing at least part of the first fibre ends, the fused first fibre ends forming at least part of the first optical interface,
determining a first active surface area for the first optical interface, the first active surface area consisting of an integral piece of area,
determining a second active surface for the second optical interface, the second active surface area consisting of an integral piece of area,
providing the fibre optic cable with a first group of optic fibres, the first active surface area including the first fibre ends of the first group of optic fibres, the second active surface area including the second fibre ends of the first group of optic fibres, each optic fibre whose first fibre end is located inside said first active surface area belonging to the first group of optic fibres, and each optic fibre whose second fibre end is located inside said second active surface area belonging to the first group of optic fibres,
providing the fibre optic cable with a second group of optic fibres, optic fibres of the second fibre group having their first fibre ends between the first active surface and an outline of the first cable end, and
arranging at least part of the optic fibres to have a noncoherent mutual arrangement between the first and second cable ends.

15. The method according to claim 14, wherein the first fibre ends at the first cable end are illuminated based on the form and size of the first active surface area and the optic fibres are separated at the second cable end into said first and second groups of optic fibres based on the illumination at each second fibre end at the second cable end.

16. The method according to claim 15, wherein the illuminating comprises applying light onto the first end of the cable and applying a mask within the optical path of the light, said mask comprising an area with a form and size of the first active surface area, within said area of the mask the transmission characteristic of the light being different from the transmission characteristic of the light outside said area of the mask.

17. The method according to claim 14, wherein:
a first fibre bundle is provided as the first group of optic fibres, and the first active surface area is formed of the first ends of the optic fibres of the first fibre bundle,
a second fibre bundle is provided as the second group of optic fibres, and the first ends of the optic fibres of the second bundle are arranged outside the first active surface area, and
the first cable end is fused for reducing the space between the individual optic fibres, the first cable end including the first ends of the optic fibres of the first fibre bundle and the first ends of the optic fibres of the second fibre bundle.

18. The method according to claim 17, wherein
the second active surface area is formed of the second ends of the optic fibres of the first fibre bundle,
second ends of the optic fibres of the second fibre bundle are arranged outside the second active surface area,
the second cable end is fused for forming the second optical interface and for reducing space between the individual optic fibres, the second cable end including the second ends of the optic fibres of the first fibre bundle and the second ends of the optic fibres of the second fibre bundle.

19. The method according to claim 14, wherein the optic fibres of the second group of optic fibres are made shorter than the fibre optic cable, whereby the second group of optic fibres serves as auxiliary optic fibres for the first cable end without extending to the second cable end.

* * * * *